United States Patent [19]

Akutsu et al.

[11] Patent Number: 4,774,367

[45] Date of Patent: Sep. 27, 1988

[54] PHENOL COMPOUND AND HEAT-SENSITIVE RECORDING MATERIAL

[75] Inventors: MItsuo Akutsu, Tokyo; Kazuhito Iuchi; Keiji Tabata, both of Saitama, all of Japan

[73] Assignee: Adeka Argus Chemical Co., Ltd., Tokyo, Japan

[21] Appl. No.: 3,751

[22] Filed: Jan. 16, 1987

[30] Foreign Application Priority Data

Jan. 21, 1986 [JP] Japan .................................. 61-10855

[51] Int. Cl.$^4$ ............................................. C07C 39/17
[52] U.S. Cl. ..................................... 568/721; 503/216; 568/731; 568/734
[58] Field of Search .................... 430/270; 503/216; 568/734, 743, 744, 747, 721, 718, 719, 720, 731

[56] References Cited

U.S. PATENT DOCUMENTS 3,000,856  9/1961  Newland et al. .................... 568/721
4,535,190  9/1985  Arai et al. ............................ 568/721

FOREIGN PATENT DOCUMENTS 1019371  2/1966  United Kingdom ................ 568/621

OTHER PUBLICATIONS

Ranson "Chemical Abstract", vol. 64 (1966), 14131d.

*Primary Examiner*—Werren B. Lone
*Attorney, Agent, or Firm*—Frishauf, Holtz, Goodman & Woodward

[57] ABSTRACT

The phenol compound of the present invention can be readily produced by, for example, reacting glyoxal, glutaraldehyde or crotonaldehyde with particular phenols. The phenol compound of the present invention is useful not only as a developer but also as an antioxidant for, e.g., synthetic resins and as an intermediate in the production of medicines or agricultural chemicals.

The heat-sensitive recording material of the present invention, which contains the phenol compound as described above, shows little discoloration of the developed color and little coloration of the ground even at a high temperature and high humidity. Thus it is highly superior to conventional ones.

6 Claims, No Drawings

PHENOL COMPOUND AND HEAT-SENSITIVE RECORDING MATERIAL

BACKGROUND OF THE INVENTION

1. Field of the Invention

This invention relates to a novel phenol compound and a heat-sensitive recording material containing the same.

2. Description of the Prior Art

A conventional process for the preparation of a heat-sensitive recording material comprises separately applying a dye, which is usually colorless or in a pale color, and a developer on the surface of a paper base together with a binder and other additives. When this recording material comes into contact with a thermal device such as a thermal head or a thermopen in a recording apparatus, the dye would react with the developer, which results in coloration in, for example, black to thereby form images.

Phenol compounds which have been employed as developers include, for example, bisphenol A, 4,4'-cyclohexylidenediphenol, 1,1,3-tris(3'-tert-butyl-4'-hydroxy-6'-methylphenyl)butane and p-hydroxybenzoate. However these phenols have disadvantages in that discoloration might be observed or that a color change might occur upon storage.

SUMMARY OF THE INVENTION

We have attempted to overcome these disadvantages and consequently found that a particular phenol compound shows an excellent effect as a developer, thus completing the present invention.

The present invention provides a phenol compound represented by the following general formula (I):

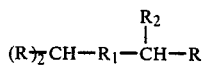 (I)

Wherein R represents a

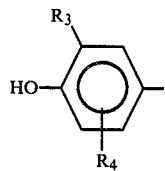

group, wherein $R_3$ represents a cyclohexyl or phenyl group and $R_4$ represents a hydrogen atom, an alkyl group having one to eight carbon atoms or those as defined in regard to $R_3$;

$R_1$ represents a direct bond or an alkylene group having one to three carbon atoms; and $R_2$ represents a hydrogen atom, an alkyl group having one to eight carbon atoms or those as defined in regard to R.

The present invention further provides a heat-sensitive recording material which comprises a dye, which is usually colorless or in a pale color, and the phenol compound of the above general formula (I).

DETAILED DESCRIPTION OF THE INVENTION

The compounds represented by the above general formula (I) include, for examples, 1,1,2,2-tetra(3'-cyclohexyl-4'-hydroxy-6'-methylphenyl)ethane, 1,1,2,2-tetra(3'-phenyl-4'-hydroxyphenyl)ethane, 1,1,3-tris(3'-cyclohexyl-4'-hydroxyphenyl)butane, 1,1,3-tris(3'-cyclohexyl-4'-hydroxy-6'-methylphenyl)butane, 1,1,3-tris(3'-cyclohexyl-4'-hydroxy-5'-methylphenyl)butane, 1,1,3-tris(3'-phenyl-4'-hydroxyphenyl)butane, 1,1,3,3-tetra(3'-phenyl-4'-hydroxyphenyl)propane, 1,1,5,5-tetra(3'-cyclohexyl-4'-hydroxy-6'-methylphenyl)pentane, 1,1,5,5-tetra(3'-cyclohexyl-4'-hydroxyphenyl)pentane and 1,1,5,5-tetra(3'-phenyl-4'-hydroxyphenyl)pentane.

The compounds of this invention can be employed as the sole color developer for heat sensitive recording paper. They can also be used in combination with other conventional color developers. The conventional color developers which can be employed together with the compound of this invention include phenols and organic acids such as p-octylphenol, p-t-butylphenol, p-phenylphenol, bisphenol A, 1,1-bis(p-hydroxyphenyl)-butane, 2,2-bis(4'-hydroxy-3',5'-dichlorophenyl)-propane, p-hydroxybenzoic acid, butyl-p-hydroxybenzoate, benzyl-p-hydroxybenzoate, 3,5-di-t-butylsalicylate, 4,4'-cyclohexylidenediphenol, p-hydroxydiphenoxide, α-naphtole, p-hydroxyacetophenone, p-t-octylcatecol, 2,2'-dihydroxybiphenyl, 2,2-bis(3'-methyl-4'-hydroxyphenyl)propane and 2,2-bis(3',5'-dimethyl-4'-hydroxyphenyl)propane.

The compounds represented by the general formula (I) can be readily prepared by reacting glyoxal, glutaraldehyde, crotonaldehyde etc, with corresponding phenols.

The color former which is normaly colorless or pale color used in this invention is not restricted. Any dye can be used provided it can be used for conventional pressure-sensitive recording paper or heat-sensitive recording paper.

Examples of such dyes includes, (1) triarylmethane compounds, for examples, 3,3-bis(p-dimethylaminophenyl)-6-dimethylaminophthalide (Crystal Violet Lactone), 3-(p-dimethylaminophenyl)-3-(1,2-dimethylindol-3-yl)phthalide, 3-(p-dimethylaminophenyl)-3-(2-phenylindol-3-yl)phthalide, 3,3-bis(9-ethylcarbazol-3-yl)-5-dimethylaminophthalide and 3,3-bis(2-phenylindol-3-yl)-5-dimethylaminophthalide; (2) diphenyl methane compounds, for example, 4,4'-bis-dimethylaminobenzhydrin benzyl ether, N-halophenyl leuco Auramine and N-2,4,5-trichlorophenyl leuco Auramine; (3) xanthene compounds, for example, Rhodamine β-anilinolactam, 3-diethylamino-7-dibenzylaminofluorane, 3-diethylamino-7-octylaminofluoran, 3-diethylamino-7(2-chloroanilino)fluoran, 3-diethylamino-6-methyl-7-anilinofluoran, 3-diethylamino-6-chloro-7-(β-ethoxyethyl)aminofluoran, 3-piperidino-6-methyl-7-anilinofluoran, 3-ethyltolylamino-6-methyl-7-anilinofluoran, 3-cyclohexylmethylanilino-6-methyl-7-anilinofluoran, 3-diethylamino-6-chlora-7-β-ethoxyethylaminofluoran and 3-diethylamino-6-chloro-7-γ-chloropropylamino-fluoran; (4) thiazine compounds, for example, benzoyl leuco Methylene Blue and p-nitrobenzoyl leuco Methylene Blue; (5) spiro compounds, for example, 3-methyl-spirodinaphthopyran, 3-ethyl-spirodinaphthopyran, 3-benzylspiro-dinaphthopyran and 3-methylnaphtho(3-methoxybenzo)spiro-pyran; and mixtures thereof.

The developer and the colorless dye as described above are atomized with an attritor such as a ball mill, an atomizer or a sand grinder or an appropriate emulsifier and various additives are added thereto depending on the purpose, thereby to form a coating solution.

This coating solution may usually contain binder(s) such as polyvinyl alcohol, hydroxyethylcellulose, methylcellulose, starch materials, styrene/maleic anhydride copolymer, vinyl acetate/maleic anhydride copolymer or styrene/butadiene copolymer; and filler(s) such as kaolin, kieselguhr, talc, titanium dioxide, calcium carbonate, magnesium carbonate or aluminum hydroxide. It may further contain other additives such as metal soaps, waxes, photostabilizers, water-resisting agents, dispersant and antifoaming agents. This coating solution is applied on the surface of papers or various films to thereby obtain the aimed heat-sensitive recording materials.

The amount of the particular phenol compound to be used in the present invention is not strictly limited and determined depending on the required properties and suitability. Generally one to ten parts of the phenol compound is employed per part of the dye.

The phenol compound of the present invention is useful not only as a developer as described above but also as an antioxidant for, e.g., synthetic resins and as an intermediate in the production of medicines or agricultural chemicals.

In the following Examples, the synthesis of the phenol compound of the present invention and heat-sensitive recording materials prepared with the use of the same will be described.

Synthetic example

Preparation of 1,1,3-tris(3'-cyclohexyl-4'-hydroxy-6'-methylphenyl)butane 2-cyclohexyl-5-methylphenol 57.0 g were dissoloved in 40 ml of methanol and 7.0 g of crotonaldehyde were added dropwise at 60°–70° C.

After addition was completed, the solution was stirred for 5 hours, while blowing hydrochloric acid gas. Then, methanol was distilled off and xylene was added and the solution was washed with water. The solution was cooled to precipitate the product. The product was filtered and white powder which melted at 212° C. was obtained.

The product was recrystallized from methanol and the pure product melted at 190° C. were obtained.

I.R. analysys
3450 cm$^{-1}$: based on hydroxyl.
1580 and 1615 cm$^{-1}$: based on aromatic ring.
1200 cm$^{-1}$: based on C-O (aromatic).

EXAMPLE 1

20 g of 3-diethylamino-6-chloro-7-anilinofluoran was atomized together with 100 g of a 10% aqueous solution of polyvinyl alcohol in a ball mill to give a dye dispersion (A).

Similarly 20 g of the sample as shown in Table 1 was atomized together with 100 g of a 10% aqueous solution of polyvinyl alcohol in a ball mill to give a dispersion (B).

The dispersions (A) and (B) were mixed together in a ratio of 3:10. To 200 g of the mixture thus obtained, 50 g of calcium carbonate was added and dispersed therein to give a coating solution.

This coating solution was applied on a base paper weighing 50 g/m$^2$ to give a coating amount of 6 g/m$^2$ on a solid basis and dried.

With the use of the heat-sensitive paper thus obtained, recording was carried out with a commercially available heat-sensitive facsimile (NEFAX-3000: mfd. by Nippon Electric Co., Ltd.) and the density of the ground and that of the developed color were measured thereafter.

The developed material was stored at 50° C., at a relative humidity of 90% and 70° C. and under a dry condition each for 48 hours. Then the density of the ground and that of the developed color were measured and the residual ratio of the developed color after the storage was determined thereby.

$$\text{Residual ratio (\%)} = \frac{\text{Density after storage}}{\text{Density before storage}} \times 100$$

Each density was measured with a Macbeth RD-514 reflective densitometer.

Table 1 shows the result.

EXAMPLE 2

20 g of 3-diethylamino-6-chloro-7-($\beta$-ethoxyethyl)aminofluoran was atomized together with 100 g of a 10% aqueous solution of polyvinyl alcohol in a ball mill to give a dye dispersion (A).

Similarly, 10 g of 2,2-bis(4-hydroxyphenyl)propane and 10 g of stearamide were atomized together with 100 g of a 10% aqueous solution of polyvinyl alcohol in a ball mill to give a dispersion (B).

Similarly 20 g of the sample compound was atomized together with 100 g of a 10% aqueous solution of polyvinyl alcohol in a ball mill to give a dispersion (C).

These dispersions (A), (B) and (C) were mixed together in a weight ratio of 3:20:5. To 200 g of the mixture thus obtained, 50 g of calcium carbonate was added and dispersed therein to give a coating solution.

This coating solution was applied on a base paper weighing 50 g/m$^2$ to give a coating amount of 6 g/m$^2$ on a solic basis and dried.

The obtained heat-sensitive paper was subjected to the same test as the one described in Example 1.

Table 2 shows the result.

TABLE-1

| No. | Sample Compound | Initial | | Moisture Resistance | | | Heat Resistance | | |
|---|---|---|---|---|---|---|---|---|---|
| | | Fog | Density | Fog | Density | Residual Ratio (%) | Fog | Density | Residual Ratio (%) |
| Comparative Example 1-1 | Bisphenol A | 0.09 | 0.93 | 0.21 | 0.68 | 73 | 0.27 | 0.72 | 77 |
| Comparative Example 1-1 | 1,1,3-Tris(3'-t-butyl-4'-hydroxy-6'-methylphenyl)butane | 0.09 | 0.92 | 0.25 | 0.73 | 79 | 0.29 | 0.75 | 82 |
| Example 1-1 | 1,1,2,2-Tetra(3'-cyclohexyl-4'-hydroxy-6'-methylphenyl)ethane | 0.09 | 0.93 | 0.15 | 0.85 | 91 | 0.18 | 0.87 | 94 |
| Example 1-2 | 1,1,3-Tris(3'-cyclohexyl-4'-hydroxy-6'-methylphenyl)butane | 0.07 | 0.93 | 0.16 | 0.86 | 92 | 0.17 | 0.88 | 95 |
| Example 1-3 | 1,1,3-Tris(3'-cyclohexyl-4'- | 0.07 | 0.93 | 0.14 | 0.85 | 91 | 0.17 | 0.87 | 94 |

TABLE-1-continued

| No. | Sample Compound | Initial Fog | Initial Density | Moisture Resistance Fog | Moisture Resistance Density | Moisture Resistance Residual Ratio (%) | Heat Resistance Fog | Heat Resistance Density | Heat Resistance Residual Ratio (%) |
|---|---|---|---|---|---|---|---|---|---|
| Example 1-4 | hydroxy-5'-methylphenyl)butane 1,1,3-Tris(3'-phenyl-4'-hydroxyphenyl)butane | 0.08 | 0.92 | 0.15 | 0.83 | 89 | 0.18 | 0.85 | 91 |
| Example 1-5 | 1,1,3,3-Tetra(3'-cyclohexyl-4'-hydroxy-6'-methylphenyl)propane | 0.07 | 0.93 | 0.15 | 0.85 | 91 | 0.17 | 0.88 | 95 |
| Example 1-6 | 1,1,3,3-Tetra(3'-phenyl-4'-hydroxyphenyl)propane | 0.09 | 0.92 | 0.16 | 0.84 | 91 | 0.18 | 0.86 | 93 |
| Example 1-7 | 1,1,5,5-Tetra(3'-cyclohexyl-4'-hydroxy-6'-methylphenyl)pentane | 0.07 | 0.93 | 0.14 | 0.86 | 92 | 0.17 | 0.87 | 94 |
| Example 1-8 | 1,1,5,5-Tetra(3'-cyclohexyl-4'-hydroxyphenyl)pentane | 0.08 | 0.92 | 0.15 | 0.85 | 92 | 0.18 | 0.86 | 93 |
| Example 1-9 | 1,1,5,5-Tetra(3'-phenyl-4'-hydroxyphenyl)pentane | 0.09 | 0.92 | 0.16 | 0.84 | 91 | 0.18 | 0.85 | 92 |

TABLE-2

| No. | Sample Compound | Initial Fog | Initial Density | Moisture Resistance Fog | Moisture Resistance Density | Moisture Resistance Residual Ratio (%) | Heat Resistance Fog | Heat Resistance Density | Heat Resistance Residual Ratio (%) |
|---|---|---|---|---|---|---|---|---|---|
| Comparative Example 2-1 | Bisphenol A | 0.07 | 0.91 | 0.14 | 0.38 | 42 | 0.11 | 0.43 | 47 |
| Comparative Example 2-1 | 1,1,3-Tris(3'-t-butyl-4'-hydroxy-6'-methylphenyl)butane | 0.07 | 0.93 | 0.13 | 0.78 | 84 | 0.12 | 0.80 | 86 |
| Example 2-1 | 1,1,2,2-Tetra(3'-cyclohexyl-4'-hydroxy-6'-methylphenyl)ethane | 0.07 | 0.92 | 0.11 | 0.85 | 92 | 0.10 | 0.86 | 93 |
| Example 2-2 | 1,1,3-Tris(3'-cyclohexyl-4'-hydroxy-6'-methylphenyl)butane | 0.06 | 0.93 | 0.10 | 0.88 | 95 | 0.07 | 0.90 | 97 |
| Example 2-3 | 1,1,3-Tris(3'-cyclohexyl-4'-hydroxy-5'-methylphenyl)butane | 0.06 | 0.93 | 0.10 | 0.87 | 94 | 0.08 | 0.89 | 96 |
| Example 2-4 | 1,1,3-Tris(3'-phenyl-4'-hydroxyphenyl)butane | 0.07 | 0.93 | 0.11 | 0.85 | 91 | 0.10 | 0.87 | 94 |

Table 1 and 2 suggest that the heat-sensitive recording materials of the present invention are highly excellent, since the developed colors thereof show little discoloration and the grounds thereof show little color development even at a high temperature and high humidity.

What is claimed is:

1. A phenol compound of the general formula (I):

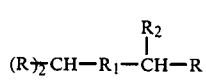
$$(R)_{\overline{2}}CH-R_1-CH-R \quad (I)$$

wherein

R represents a

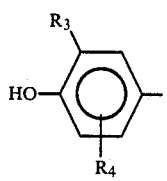

-group, wherein

R₃ represents a cyclohexyl or phenyl group, and R₄ represents a hydrogen atom, an alkyl group having one to eight carbon atoms, cyclohexyl or phenyl group;

R₁ represents a direct bond or an alkylene group having one to three carbon atoms; and R₂ represents a hydrogen atom, an alkyl group having one to eight carbon atoms or a

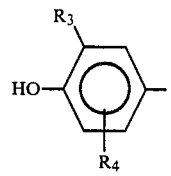

-group, wherein

R₃ represents a cyclohexyl or phenyl group, and R₄ represents a hydrogen atom, an alkyl group having one to eight carbon atoms, cyclohexyl or phenyl group.

2. The phenol compound as set forth in claim 1, wherein

R is a

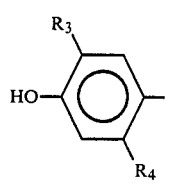

-group,

R₃ is a cyclohexyl group;
R₄ is a methyl group;
R₁ is a methylene group; and
R₂ is a methyl group.

3. A heat-sensitive recording material comprising a dye, which is colorless or in a pale color, and a phenol compound of the formula (I):

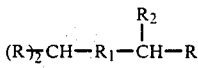

wherein
R represents a

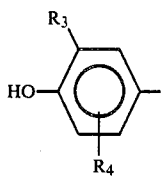

-group, wherein $R_3$ represents a cyclohexyl or phenyl group, and $R_4$ represents a hydrogen atom, an alkyl group having one to eight carbon atoms, cyclohexyl or phenyl group;

$R_1$ represents a direct bond or an alkylene group having one to three carbon atoms; and $R_2$ represents a hydrogen atom, an alkyl group having one to eight carbon atoms or a

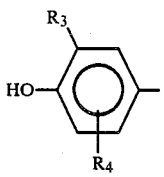

-group, wherein $R_3$ represents a cyclohexyl or phenyl group, and $R_4$ represents a hydrogen atom, an alkyl group having one to eight carbon atoms, cyclohexyl or phenyl group.

4. The heat-sensitive recording material as set forth in claim 3, wherein said phenol compound is 1,1,3-tris(2-methyl-4-hydroxy-5-cyclohexylphenyl)butane.

5. The phenol compound as set forth in claim 1, selected from the group consisting of 1,1,2,2-tetra(3'-cyclohexyl-4'-hydroxy-6'-methylphenyl)ethane, 1,1,2,2-tetra(3'-phenyl-4'-hydroxyphenyl)ethane, 1,1,3-tris(3'-cyclohexyl-4'-hydroxyphenyl)butane, 1,1,3-tris(3'-cyclohexyl-4'-hydroxy-6'-methylphenyl)butane, 1,1,3-tris(3'-cyclohexyl-4'-hydroxy-5'-methylphenyl)butane, 1,1,3-tris(3'-phenyl-4'-hydroxyphenyl)butane, 1,1,3,3-tetra(3'-phenyl-4'-hydroxyphenyl)propane, 1,1,5,5-tetra(3'-cyclohexyl-4'-hydroxy-6'-methylphenyl)pentane, 1,1,5,5-tetra(3'-cyclohexyl-4'-hydroxyphenyl)pentane and 1,1,5,5-tetra(3'-phenyl-4'-hydroxyphenyl)pentane.

6. The heat sensitive recording material as set forth in claim 3, wherein the said phenol compound is selected from the group consisting of 1,1,2,2-tetra(3'-cyclohexyl-4'-hydroxy-6'-methylphenyl)ethane, 1,1,2,2-tetra(3'-phenyl-4'-hydroxyphenyl)ethane, 1,1,3-tris(3'-cyclohexyl-4'-hydroxyphenyl)butane, 1,1,3-tris(3'-cyclohexyl-4'-hydroxy-6'-methylphenyl)butane, 1,1,3-tris(3'-cyclohexyl-4'-hydroxy-5'-methylphenyl)butane, 1,1,3-tris(3'-phenyl-4'-hydroxyphenyl)butane, 1,1,3,3-tetra(3'-phenyl-4'-hydroxyphenyl)propane, 1,1,5,5-tetra(3'-cyclohexyl-4'-hydroxy-6'-methylphenyl)pentane, 1,1,5,5-tetra(3'-cyclohexyl-4'-hydroxyphenyl)pentane and 1,1,5,5-tetra(3'-phenyl-4'-hydroxyphenyl)pentane.

* * * * *